(12) United States Patent
Rice

(10) Patent No.: US 7,921,727 B2
(45) Date of Patent: Apr. 12, 2011

(54) SENSING SYSTEM FOR MONITORING THE STRUCTURAL HEALTH OF COMPOSITE STRUCTURES

(75) Inventor: Brian P. Rice, Mason, OH (US)

(73) Assignee: University of Dayton, Dayton, OH (US)

(*) Notice: Subject to any disclaimer, the term of this patent is extended or adjusted under 35 U.S.C. 154(b) by 990 days.

(21) Appl. No.: 11/166,056

(22) Filed: Jun. 24, 2005

(65) Prior Publication Data

US 2005/0284232 A1 Dec. 29, 2005

Related U.S. Application Data

(60) Provisional application No. 60/583,239, filed on Jun. 25, 2004.

(51) Int. Cl.
*G01B 11/16* (2006.01)
(52) U.S. Cl. .......................................... 73/762
(58) Field of Classification Search .................. 73/762, 73/763, 766, 774, 777, 795, 805
See application file for complete search history.

(56) References Cited

U.S. PATENT DOCUMENTS

| | | | |
|---|---|---|---|
| 4,506,250 A | 3/1985 | Kirby | |
| 4,708,019 A * | 11/1987 | Rubner et al. | 73/760 |
| 4,732,042 A * | 3/1988 | Adams | 73/706 |
| 5,175,214 A * | 12/1992 | Takaya et al. | 525/104 |
| 5,302,936 A * | 4/1994 | Yaniger | 338/47 |
| 5,512,131 A * | 4/1996 | Kumar et al. | 438/738 |
| 5,541,570 A * | 7/1996 | McDowell | 338/47 |
| 5,817,944 A * | 10/1998 | Chung | 73/768 |
| 5,843,155 A * | 12/1998 | Axelgaard | 607/152 |
| 5,904,712 A * | 5/1999 | Axelgaard | 607/148 |
| 5,989,700 A | 11/1999 | Krivopal | |
| 6,276,214 B1 | 8/2001 | Kimura et al. | |
| 6,418,333 B1 * | 7/2002 | Axelgaard | 600/391 |
| 6,643,532 B2 * | 11/2003 | Axelgaard | 600/391 |
| 6,680,016 B2 | 1/2004 | Wang et al. | |
| 6,922,179 B2 * | 7/2005 | McCollum | 343/895 |
| 6,964,205 B2 * | 11/2005 | Papakostas et al. | 73/862.046 |
| 6,986,287 B1 * | 1/2006 | Dorfman | 73/776 |
| 7,007,553 B2 * | 3/2006 | Kinoshita et al. | 73/777 |
| 7,106,208 B2 * | 9/2006 | Devos | 340/686.1 |
| 7,116,209 B2 * | 10/2006 | Hermann et al. | 338/2 |
| 7,151,129 B2 * | 12/2006 | Ishikawa et al. | 524/414 |
| 7,151,528 B2 * | 12/2006 | Taylor et al. | 345/168 |
| 2003/0039816 A1 * | 2/2003 | Wang et al. | 428/299.1 |
| 2004/0239475 A1 * | 12/2004 | Hermann et al. | 338/25 |
| 2005/0073744 A1 * | 4/2005 | Zheludev et al. | 359/489 |
| 2005/0145045 A1 * | 7/2005 | Papakostas et al. | 73/864 |
| 2005/0268699 A1 * | 12/2005 | Papakostas et al. | 73/46 |

FOREIGN PATENT DOCUMENTS

| | | |
|---|---|---|
| GB | 2 202 636 A | 9/1988 |
| WO | WO 03/018307 A1 | 3/2003 |

* cited by examiner

*Primary Examiner* — Lisa M Caputo
*Assistant Examiner* — Freddie Kirkland, III
(74) *Attorney, Agent, or Firm* — Dinsmore & Shohl LLP

(57) ABSTRACT

A sensing system for use in monitoring the structural health of a structure such as a polymeric matrix composite structure is provided. The system includes a sensor formed from a conductive ink containing carbon nanofibers and a polymeric resin, and a data acquisition system for acquiring and evaluating data from the sensor. The conductive ink may be applied directly to the structure to be monitored in the form of a grid pattern. Damage to the structure may be detected by measuring changes in resistance values detected from the sensor.

15 Claims, 7 Drawing Sheets

SENSING SYSTEM FOR MONITORING THE STRUCTURAL HEALTH OF COMPOSITE STRUCTURES

CROSS REFERENCE TO RELATED APPLICATIONS

This application claims the benefit of U.S. Provisional Application No. 60/583,239, entitled SENSOR FOR MONITORING THE STRUCTURAL HEALTH OF COMPOSITE STRUCTURES, filed Jun. 24, 2004. The entire contents of said application are hereby incorporated by reference.

GOVERNMENT RIGHTS

The government has rights in the invention pursuant to Contract No. 200-18-14W36063 awarded by GE Aircraft Engines/NASA Glenn.

BACKGROUND OF THE INVENTION

The present invention relates to a sensing system used to monitor the structural health of structures such as polymeric matrix composite structures, and more particularly, to a sensor which utilizes a conductive ink incorporating carbon nanofibers which may be applied to a structure.

Monitoring the structural health of structures which are used over long periods of time has become increasingly important. Over time, structures such as architectural and vehicular structures as well as aircraft, turbine blades, bridges, satellites, and ships can suffer from defects such as fractures and fatigue cracks. Such defects, if undetected, may result in dangerous accidents. Currently, the monitoring of such structures is time consuming and expensive. This is particularly evident where the structures to be monitored must be disassembled and transported to testing facilities. Detecting hidden defects without disassembly of the structures is even more difficult when the structures cannot be disassembled, for example, in the case of buildings and bridges.

Conventional strain gages are known in the art but are not appropriate for monitoring the structural health of large structures as they cover a relatively small sensing area of up to several inches and require sophisticated calibration and electronics to monitor the strain. A more recent monitoring approach has been the development of a strain sensor which uses conductive particles dispersed in a polymer. This strain sensor has shown significant promise for monitoring gross deformation in civil structures. See, for example, U.S. Pat. No. 6,276,214. However, in use, the sensor must be adhered to a film which is then adhesively bonded to a structure. Such a system requires a durable adhesive in order to ensure that the sensor does not peel off over time. In addition, such a sensor may be difficult to apply to rough or uneven surfaces.

Accordingly, there is a need in the art for a sensor which can quickly and easily monitor the structural health of structures such as composite structures, which can be applied to complex contours, and which is environmentally durable.

SUMMARY OF THE INVENTION

The present invention meets that need by providing a sensing system for monitoring the structural health of structures such as aircraft, bridges, and buildings which utilizes a sensor comprising a conductive ink having controllable electrical and mechanical properties. The sensor may be applied directly to a structure in any desired pattern as needed to monitor structural damage and strain of the structure. The sensor can be easily adhered to a variety of surfaces and may be tailored to detect damage at specific strain levels. The sensor has a very high signal to noise ratio, and utilizes conventional electrical resistance measurement conducive to multiplexing of plural sensors such as may be found in a sensing grid covering a large area. The sensor may be applied directly to a structure either manually or using automated equipment. The sensor has little effect on the surface profile of the structure, and adds very little weight to the structure.

According to one aspect of the present invention, a sensing system for monitoring the structural health of a structure is provided comprising a sensor comprising a conductive ink containing carbon nanofibers and at least one polymeric resin. The sensing system further comprises a data acquisition system for acquiring and evaluating data retrieved from the sensor. Preferably, the data acquisition system comprises electrodes bonded to the sensor and a voltage meter. The electrodes are preferably bonded to the ends of the individual conductive ink grid lines making up the sensor and wires extending from the electrodes are connected to the voltage meter.

The conductive ink preferably comprises from about 4 to about 12% by weight carbon nanofibers and a polymeric resin selected from the group consisting of epoxy resins, polyimides, bismaleimides, cyanate esters, polyesters, vinyl esters, and urethanes.

Types of structures to which the sensor may be applied include polymeric matrix composite structures, metal structures, or concrete structures. Where the structure comprises a polymeric matrix composite structure, the polymeric resin in the conductive ink is preferably compatible with the polymer in the polymeric matrix composite structure. By "compatible," it is meant that the polymer used in the ink has similar mechanical, chemical, and thermal properties as that of the polymer contained in the composite structure. Accordingly, the conductive ink will degrade in relation to the structure being monitored, based on the environment the structure is used in. More preferably, the polymeric resin in the conductive ink is the same as the polymer in the polymeric matrix composite structure.

In the method of using the sensing system, the sensor is applied to the structure to be monitored, preferably by painting, rolling, or spraying. The sensor may be applied directly to the structure. However, in instances where the structure to be monitored is electrically conductive, it is preferable that a nonconductive insulating coating be applied to the structure prior to and/or after application of the sensor so as to electrically isolate the structure from the sensor.

The sensor is preferably applied in the form of a grid pattern to the structure to be monitored. When the structure to be monitored exhibits damage or cracks, the data acquisition system which is connected to the sensor senses an open circuit and/or an increase in resistance at the particular grid lines where the damage/cracks have occurred.

Accordingly, it is a feature of the present invention to provide a sensing system for monitoring the structural health of a composite structure which utilizes a sensor comprising a conductive ink which is applied to the structure and a data acquisition system. Other features and advantages of the invention will be apparent from the following description, the accompanying drawings, and the appended claims.

DETAILED DESCRIPTION OF THE INVENTION

Figure 1:
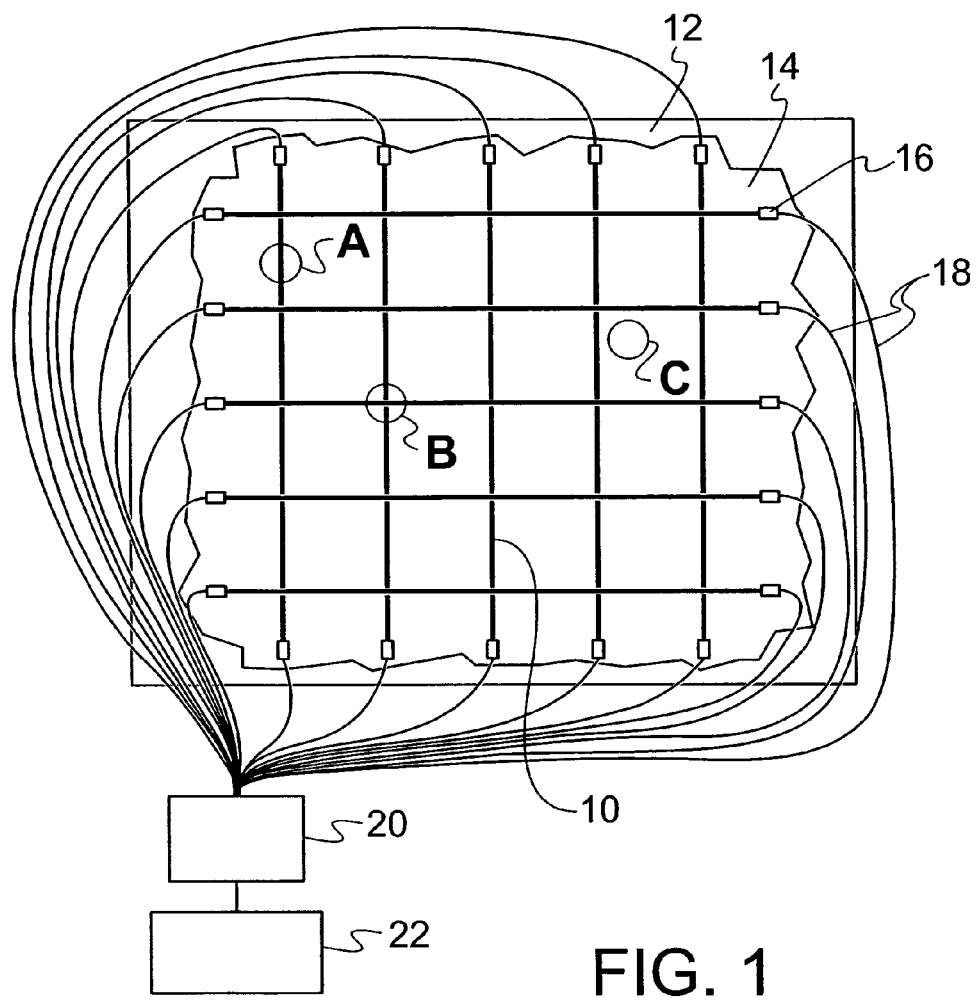
FIG. 1 is a schematic illustration of a sensing system in accordance with an embodiment of the present invention.

The sensor of the present invention utilizes a conductive ink containing carbon nanofibers which may be tailored for strains of failure of over 100%, depending on the particular ink formulation. This provides a significant advantage over previous monitoring systems which cannot be tailored for specific strain requirements. We have found that by using inks formulated with modest loadings of highly conductive carbon nanofibers, the inks provide a robust sensing capability over a broad strain range. The high aspect ratio of the nanofibers contributes to the low loading levels required to achieve the desired level of conductivity needed for the sensor. It should be appreciated that while carbon nanofibers have been described for use in the ink, it may be possible to use other nano-materials such as carbon nanotubes as long as they possess the required high aspect ratio and good dispersion.

The conductive ink which forms the sensor may be formulated from a variety of polymeric resins. Where the ink is applied to a polymeric matrix composite, the ink preferably contains the same polymeric matrix resin as the composite to ensure proper compatibility. By selecting a compatible resin, this ensures good adhesion of the sensor to the structure, and ensures that the rate of environmental degradation of the structure is similar to that of the sensor. Polymeric matrix composites to which the ink may be applied include, but are not limited to, carbon fiber/epoxy composites, glass/vinyl ester composites, etc. It should be appreciated that there are many combinations of materials that may form a polymeric matrix composite structure.

As many aerospace composite structures are fabricated from epoxy resins, epoxy resins are preferred for use in the ink. Other suitable resins include, but are not limited to, polyimides, bismaleimides, cyanate esters, polyesters, vinyl esters, urethanes, and any other polymers which can be solvated to reduce viscosity. It should be appreciated that any resin which is used to fabricate structures is suitable for use in the present invention. The selection of polymeric resins should be based on strain requirements for the structure to be monitored as well as exposure to environmental conditions such as chemicals or extreme temperatures.

The amount of nanofibers included in the conductive ink is preferably chosen to provide a balance between electrical resistance (less fiber, higher resistance) and viscosity (more fiber, higher viscosity). The conductive ink preferably includes a nanofiber loading of from about 4 to about 12 wt %. The conductive ink is preferably made using the process described in U.S. Pat. No. 6,680,016, the disclosure of which is hereby incorporated by reference. The process includes dispersing carbon nanofibers or other conductive nanoparticles in a solvent and adding a (thermoplastic) polymer to form a substantially homogeneous dispersion. Excess solvent is then removed via evaporation.

Alternatively, when thermoset polymers are used in the ink formulation, an appropriate curing agent or catalyst may be added, and if necessary, elevated temperatures may be used to cure the ink once it has been applied to the structure. If the structure to be monitored is to be painted, it may be painted after the ink has been applied and cured.

Referring now to FIG. 1, the sensing system of the present invention is illustrated. The system includes a sensor 10 comprising the conductive ink which is applied in the form of a grid to a composite structure 12. In the embodiment shown, the grid is made up of five vertical and five horizontal lines, (5×5 grid).

Because many composite structures are electrically conductive, the grid lines are preferably electrically isolated from each other by the application of a thin, nonconductive insulating coating 14 onto the structure which forms a polymeric film. The coating 14 is preferably applied so as to cover the surface area of the composite over which the sensor grid will be applied. The nonconductive coating preferably comprises the same resin contained in the conductive ink (such as epoxy), and is preferably painted or sprayed onto the composite before and after the first set of grid lines are applied so as to isolate any intersecting grid lines. Thus, the sensor grid is electrically isolated from the composite structure 14 and the intersecting horizontal/vertical lines are also isolated.

The conductive ink is painted, rolled or sprayed onto composite structure 14 using a line spacing which is consistent with the required spatial resolution for damage detection. Preferably, a mask or template is positioned on the composite prior to application of the conductive ink which defines the sensor line width/length. The template may take the form of a sheet with cutouts defining the ink lines or may be applied as parallel strips of tape. The template may be removed after application of the conductive ink. For example, in a typical method of applying the sensor, the method includes 1) applying the insulating coating to the structure; 2) applying a (horizontal) template; 3) applying the conductive ink (to form horizontal grid lines); 4) removing the horizontal template; 5) applying the insulating coating over the horizontal grid lines/structure; 6) applying a (vertical) template; 7) applying the conductive ink (to form vertical grid lines); and 8) removing the vertical template.

While the sensor is preferably applied in the form of a grid pattern as shown, it should be appreciated that the sensor may be applied in a variety of patterns which are tailored to yield the desired information regarding the structure. For example, in its simplest form, the sensor may be provided in the form of a single line.

Once applied, the electrical conductivity of the conductive ink changes as a function of applied strain and damage. The strain and conductivity characteristics of the ink may be modified according to the particular structure being monitored. The method of monitoring the electrical conductivity may be performed either manually or automatically. A conventional data acquisition system which is capable of reading a DC voltage may be used to acquire data. The preferred data acquisition system comprises conventional electrodes 16 (such as those having a pinch blade configuration) which are bonded to the ends of each sensor grid line as shown. Wires 18 are then plugged into the electrode and a volt meter or other measuring device 20 is used to measure the electrical resistance across the wires. Data may then be analyzed using conventional equipment such as a computer 22.

However, it should be appreciated that any device capable of monitoring resistance in either a qualitative or quantitative manner may be used in the practice of the present invention. For example, a circuit comprising a light bulb and battery where the sensor grid completes the circuit could be used. A dim or unlighted bulb would indicate a damaged section of the grid and structure.

While the sensor of the present invention is primarily for use in monitoring the structural health of polymeric matrix composites, it may also be used to monitor other structures including metal and concrete structures. However, special care must be taken to ensure that the surfaces of such structures are properly prepared to ensure durable adhesion of the ink to the surface, i.e., the surface should be free of dust, dirt, loose materials, grease, etc.

The sensor may be applied to structures which are provided in a variety of forms including uni-tape lay-ups, laminates fabricated from braids, and sandwich structures, including flat and curved structures. The sensing system may be used on prototype structures to evaluate structural performance during testing, as well as for applications where component inspection is impractical, such as buried structures, and structures in remote locations. The system may be used on aircraft, spacecraft, bridges, pipelines, wind turbines, ships, buildings, and the like.

In use, when the sensing system is applied to a structure, the vertical and horizontal lines of the grid may be used to locate damage by an increase in resistance which occurs during or after damage. Where damage occurs along, for example, a vertical sensor line on the grid (shown as point A in FIG. 1), the sensor line would yield an open circuit indicating the horizontal position of the damage. Adjacent horizontal lines may be used to locate vertical damage if a slight resistance increase is detected during or after the damage event. Generally, the risk of damage progression resulting from increased strain levels surrounding a damaged zone is of primary concern. The sensor applied in the form of a grid provides the ability to detect this increase in strain level.

Where the damage location is at an intersection of horizontal and vertical grid lines as shown at point B, an increased level of resistance would occur.

Where the damage location occurs within the grid (see point C), i.e., away from direct contact with a horizontal or vertical line, damage may still be detected by increased strain levels of the bordering sensor lines. However, it is preferable to minimize the grid spacing to detect small damage levels. The sensor grid layout can be easily optimized through finite element stress analysis given the safety factor of the design and calculation of critical damage size.

It should be noted that if damage to a structure occurs which is repairable, it is possible to restore the sensor grid in the area where the damage occurred. By sanding a small section of undamaged grid line, a new grid line may be applied on the repaired structure with good electrical contact. If desired, the grid pattern could even be changed to monitor the repaired area with higher resolution. This type of flexibility is not possible with embedded sensors such as fiber optics.

Figure 2:
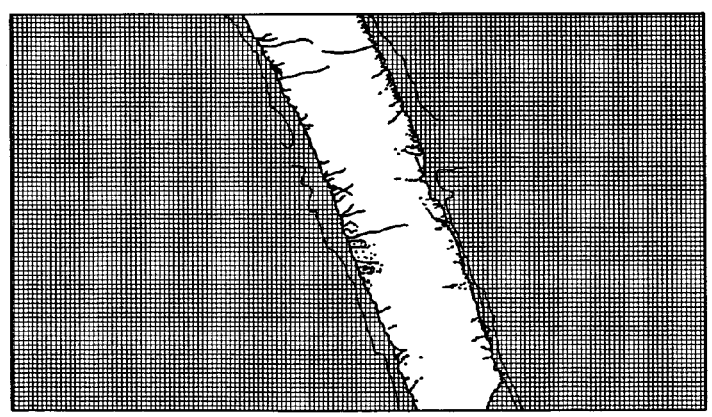
FIG. 2 is an enlarged schematic view of a sensor applied to a composite structure containing a crack therein and illustrating carbon nanofibers extending across the crack.

It should also be noted that the conductive ink should be formulated so that it begins to crack at the same strain level as the underlying structure. For example, a crack in the composite should also cause the sensor grid to begin to crack. See FIG. 2, which illustrates an enlarged view of a conductive ink grid line which has been applied to a structure containing a crack. As shown, the grid line is also cracked such that the conductive nanofibers extend across the gap. It should be noted that when the crack closes at normal strain levels, the protruding fibers make electrical contact once again but at a reduced level. The sensor grid of the present invention provides an advantage over previous conductive ink sensor grids because it is possible to infer much more information about the damage state. In addition, the nanofibers actually strengthen the conductive ink unlike previous conductive inks, which tend to be weak and brittle.

In order that the invention may be more readily understood, reference is made to the following examples which are intended to illustrate the invention, but not limit the scope thereof.

EXAMPLE 1

Figure 3:
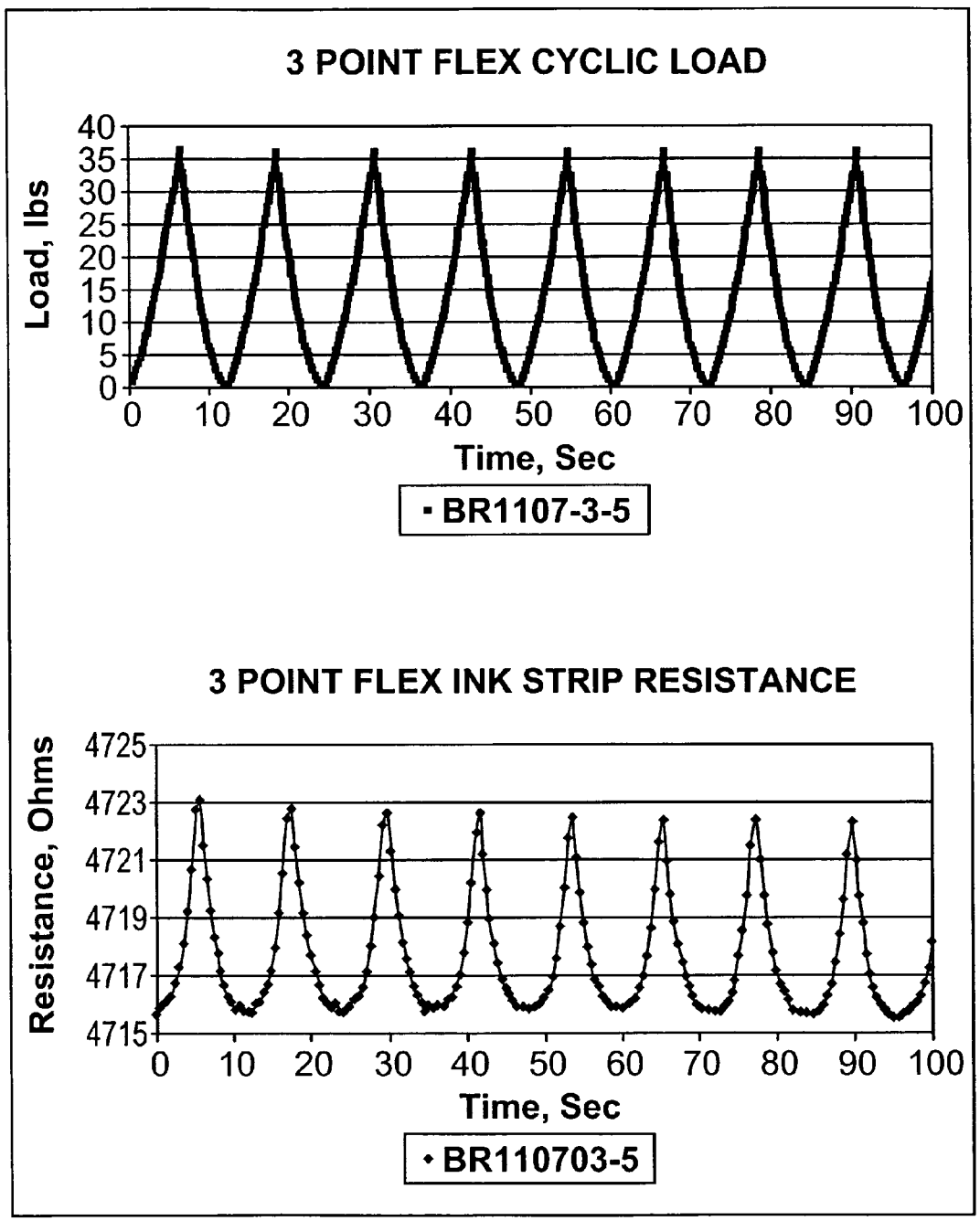
FIG. 3 is a graph illustrating load and resistance curves of a composite laminate during a cyclic flex test where the sensor is applied on the bottom surface.

A 1"×6" carbon fiber/epoxy composite laminate was subjected to a cyclical three point bend test in which the sample was loaded to 35 pounds then unloaded in a sinusoidal pattern. FIG. 3 illustrates the correlation between structural strain and changes in resistance. As can be seen, the sensor grid line resistance increases with applied load and returns to the initial resistance when the applied load is zero. With this small loading level, the resistance increases from an initial value of 4715 ohms to a value of 4723 ohms. Resistance levels rise to over 100 k-ohms when the sensor grid develops permanent cracks, so the sensing system is very sensitive over a wide range of strain values. It should be noted that after 100 cycles at approximately 2% strain, the sensor grid was still intact.

EXAMPLE 2

Figure 4:
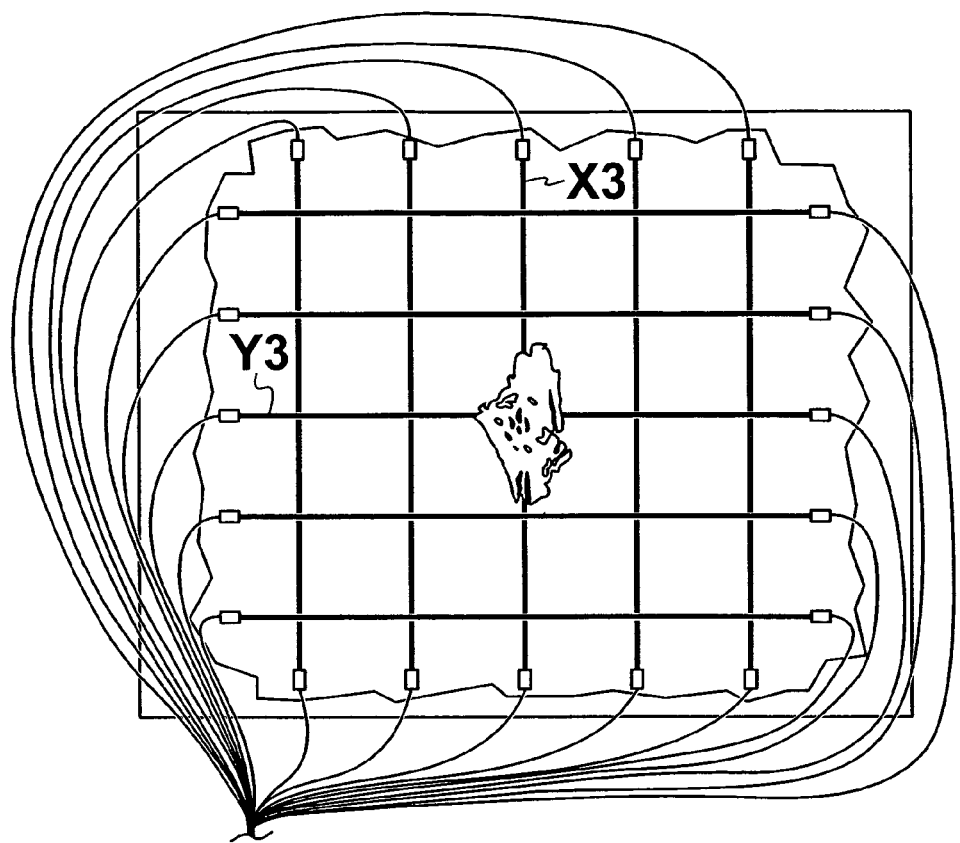
FIG. 4 is a schematic illustration of a sensor grid on a laminate after penetration of the laminate with a one inch indentor.
Figure 5A:
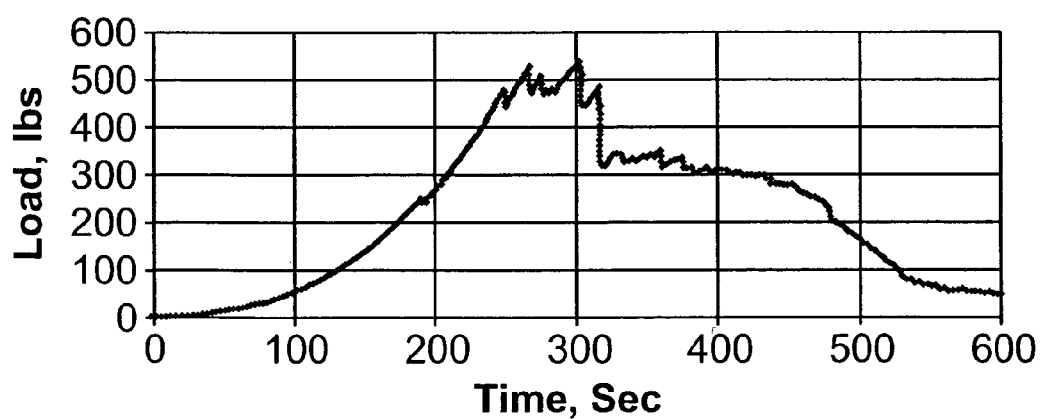
FIGS. 5A-5F are a series of graphs illustrating resistance values for the X gridlines of the sensor of FIG. 4.
Figure 5B:
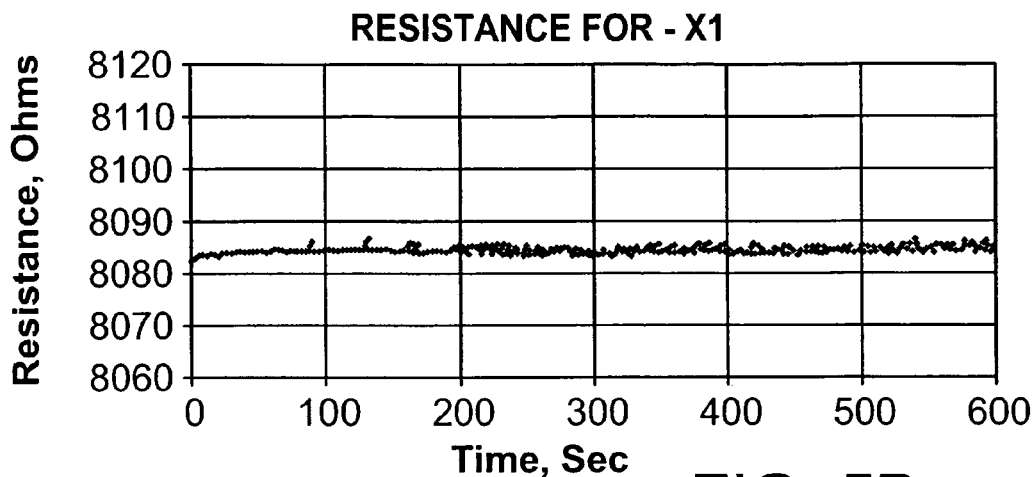
Figure 5C:
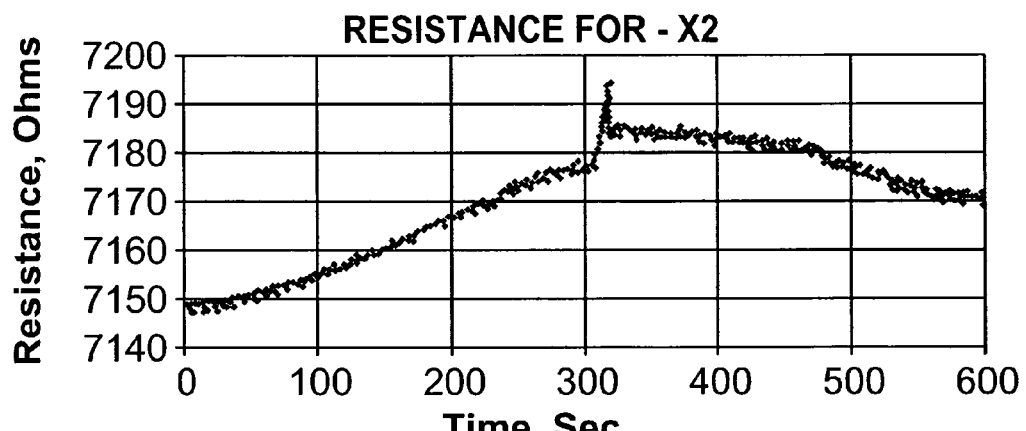
Figure 5D:
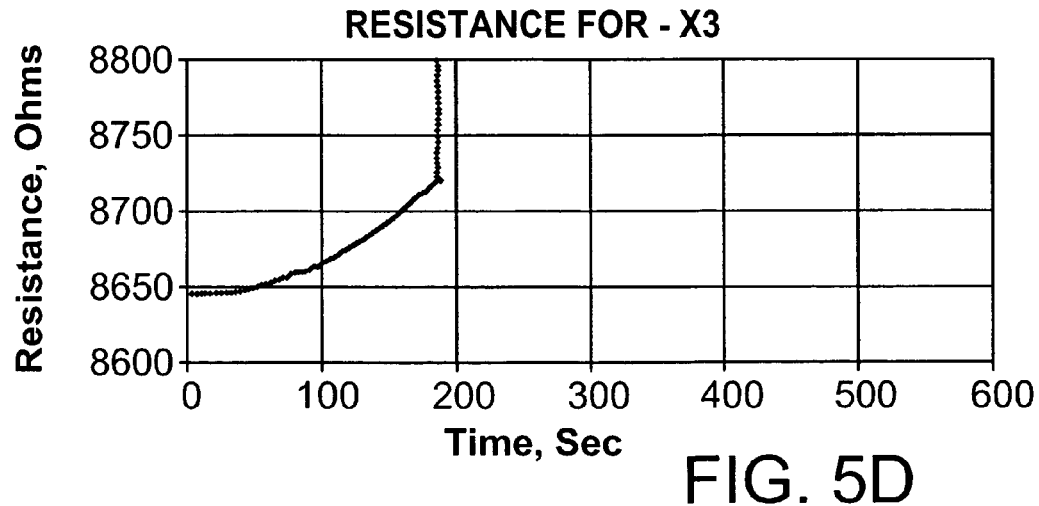
Figure 5E:
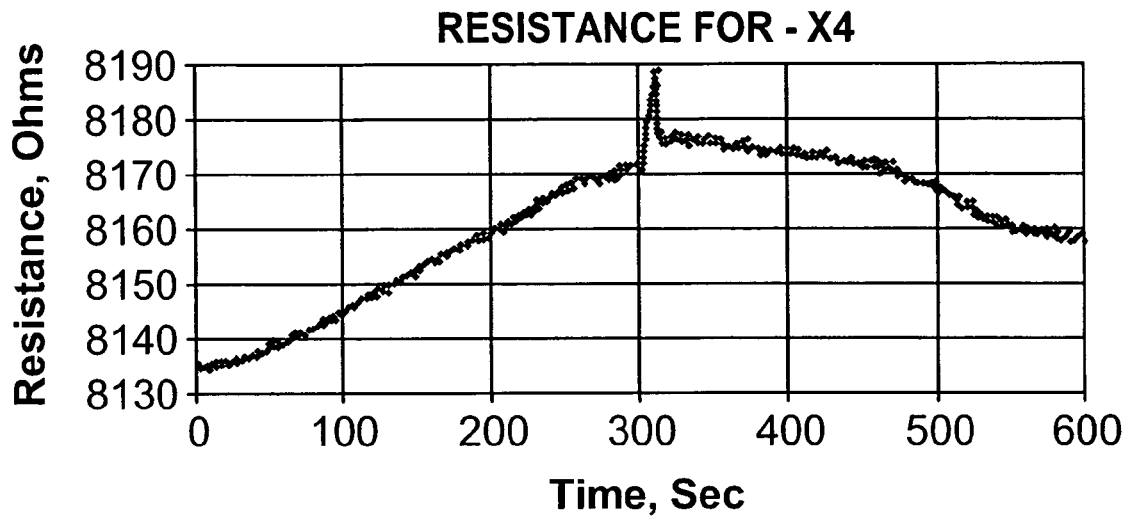
Figure 5F:
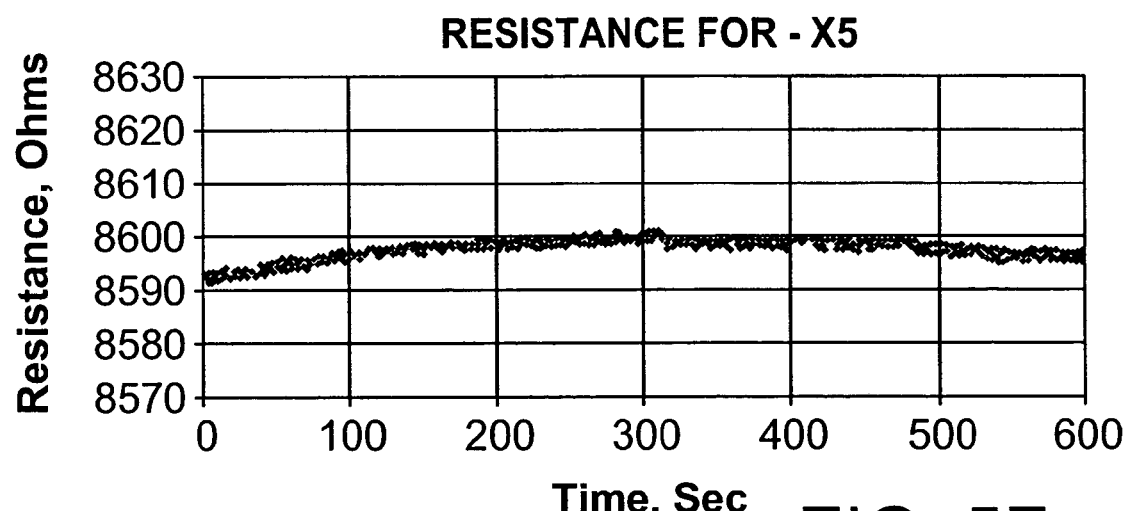

A 5"×5" sensor grid was applied to a 12"×12" carbon fiber/epoxy composite laminate. The grid lines had a spacing of two inches and were electrically isolated from each other. The laminate was supported with a ten inch diameter ring and a one inch diameter indentor was used to penetrate the laminate at the intersection of sensor lines X3 and Y3 as illustrated in FIG. 4. The circuits at X3 and Y3 were broken. Real-time data traces of indentor load and X-grid resistance values are shown in FIGS. 5A-5F. The load increases gradually as does the resistance value of X3. Resistance values of X2 and X4 also increase but at a reduced rate. Grid lines X1 and X5 which are supported almost entirely by the test ring show almost no change during the test. At 190 seconds there is an inflection in the load curve and X3 rapidly goes off scale. This is the time when the indentor tip pops through the plate. The loading continues and the indentor continues to punch through the plate as the load increases. The resulting plate deflection results in increased strain on the sensor lines which drives up the resistance values of X2 and X4. At 310 seconds, the plate deflection has reached its maximum when the indentor tip has broken through completely. As the indentor cylinder continues to punch through the hole in the plate the load and X2 and X4 resistance values decrease.

EXAMPLE 3

Figure 6:
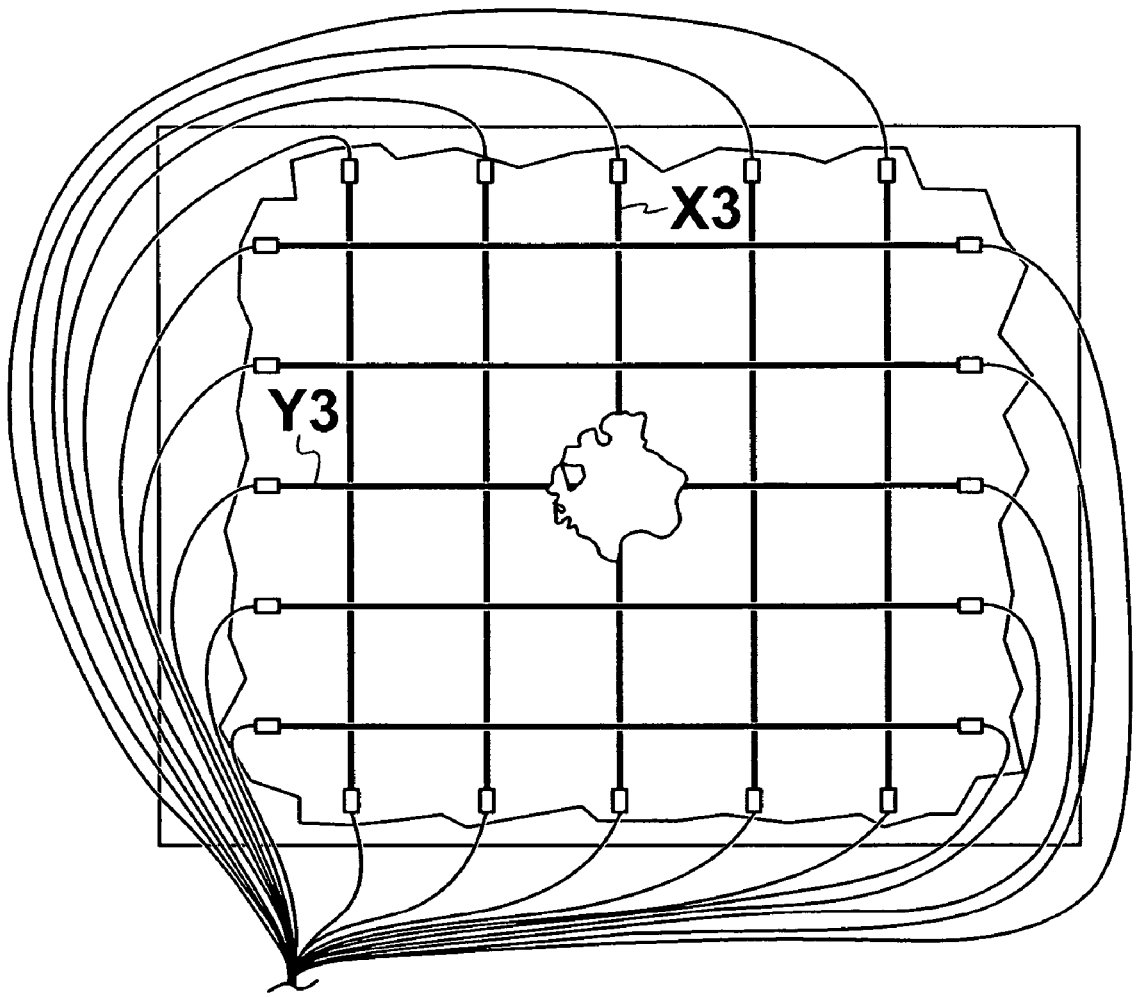
FIG. 6 is a schematic illustration of a sensor grid on a laminate after an impact test using a steel ball projectile traveling at 1000 ft/s.

A dynamic impact test was conducted on a 12"×12" carbon fiber/epoxy/foam sandwich structure with a 5"×5" sensor grid applied on its surface. A ⅞ inch diameter steel ball was shot with a velocity of 1000 feet/second at the sandwich panel which was supported by a circular ring. The ball was aimed at the intersection of sensor lines X3 and Y3 as depicted in FIG. 6. Resistance readings for all ten sensor lines were recorded at a frequency of 1 Mhz. The damage zone was limited to a diameter of approximately two inches. The carbon tow which makes up the braided structure of the sandwich skin still filled most of the damage zone, acting as tiny conductive brushes. It was noted that the sensor grid lines were still intact outside the damaged zone, which is an improvement over prior methods in which strain gages or other sensors fail when shock waves cause the sensor to pop off.

Figure 7:
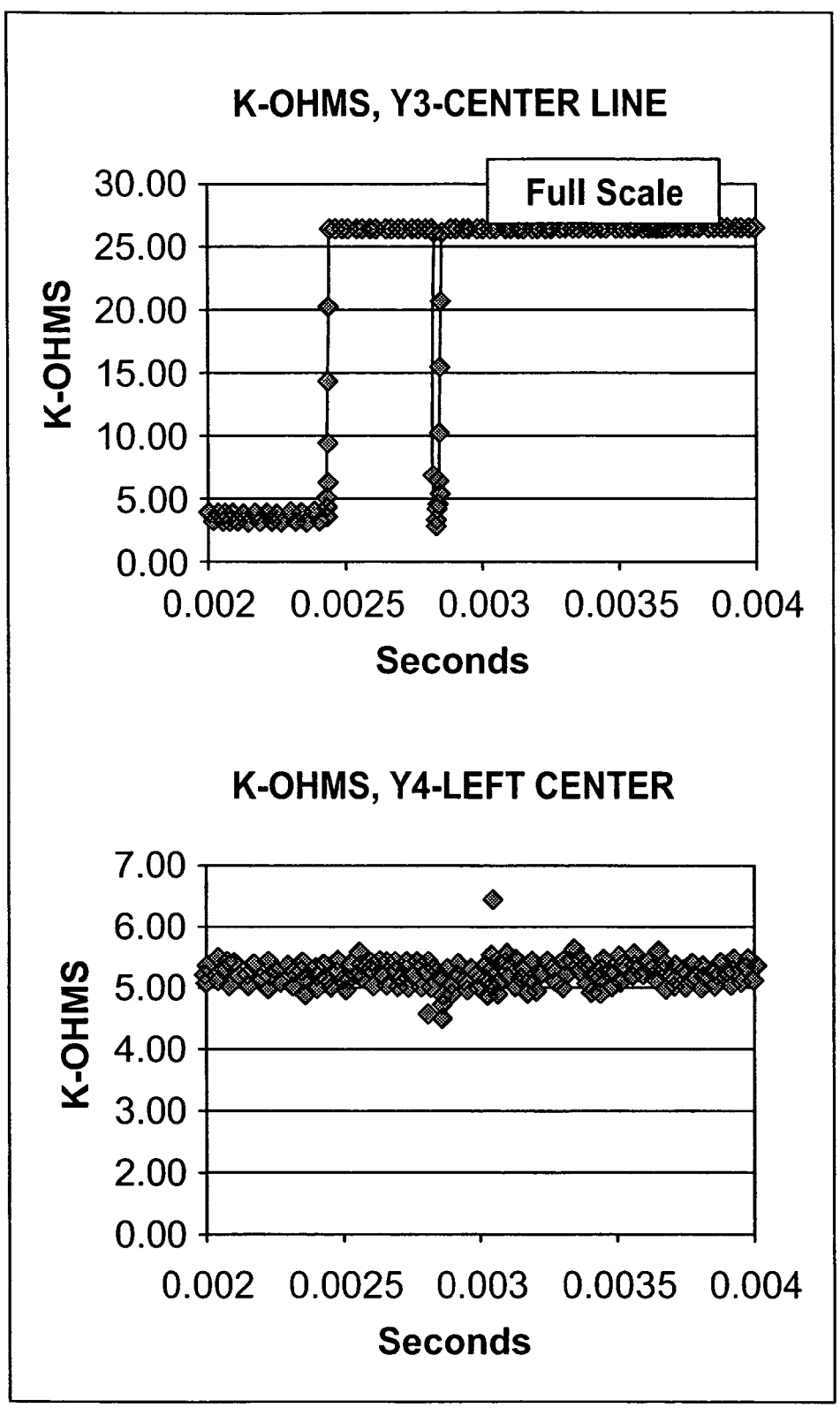
FIG. 7 is a series of graphs illustrating resistance readings from the sensor during the impact test.

FIG. 7 shows the resistance reading of Y3 (impact site) and Y4 (nearest to impact). The resistance value of Y3 was unchanged until impact occured on the opposite skin at 0.0024 seconds. The strain or bulge at the impact site caused the resistance to rise rapidly and exceed the data acquisition threshold value of 26 k-ohms. The resistance value remained off-scale until a sudden dip occurred at 0.0028 seconds. This is the period when the steel ball is passing through the second skin with the sensor grid. The broken carbon fiber tows made electrical contact with the ball, thus completing the sensor grid circuit for 0.05 milliseconds. Once the ball passed through the plate, the resistance reading was off-scale once again. The resistance value for Y4 was unchanged (as well as all the other surrounding grid lines) and visual inspection confirmed there was no structural damage crossing into Y4. Real-time data acquisition illustrates how useful this grid is to study dynamic events. Static readings of all ten sensor lines are shown in Table 1 below.

TABLE 1

| Branch code | Average resistance before shooting (Ohm) | Average resistance after shooting (Ohm) |
|---|---|---|
| X1 | 4024 | 3844 |
| X2 | 2615 | 3984 |
| X3 | 4663 | 72792 |
| X4 | 4362 | 4192 |
| X5 | 5571 | 5051 |
| Y1 | 2555 | 2563 |
| Y2 | 3688 | 3640 |
| Y3 | 3534 | infinity |
| Y4 | 4523 | 5400 |
| Y5 | 4087 | 3952 |

As can be seen, there was little change to the resistance values aside from X3 and Y3. X3 still maintained some measurable level of resistance (73 k-ohms) because of the interaction with the conductive carbon fibers surrounding the damage zone.

Having described the invention in detail and by reference to preferred embodiments thereof, it will be apparent that modifications and variations are possible without departing from the scope of the invention.

The invention claimed is:

1. A sensing system for monitoring the structural health of a structure comprising:
a sensor comprising a conductive ink containing from about 4 to about 12% by weight vapor grown carbon nanofibers having a high aspect ratio and at least one polymeric resin; and
a data acquisition system; wherein said sensor is applied in the form of a grid pattern directly to the surface of said structure.

2. The system of claim 1 wherein said data acquisition system comprises electrodes bonded to said sensor.

3. The system of claim 2 wherein said data acquisition system further includes a voltage meter.

4. The system of claim 1 wherein said structure is selected from a polymeric matrix composite structure, a metal structure, or a concrete structure.

5. The system of claim 1 wherein said structure comprises a polymeric matrix composite structure, and wherein said polymeric resin in said conductive ink is compatible with the polymer in said polymeric matrix composite structure.

6. A sensing system for monitoring the structural health of a polymeric matrix composite structure comprising:
a sensor comprising a conductive ink containing from about 4 to about 12% by weight vapor grown carbon nanofibers having a high aspect ratio and at least one polymeric resin which is compatible with said polymer in said polymeric matrix composite structure; and
a data acquisition system.

7. A method of monitoring the structural health of a structure comprising:
providing a sensor comprising a conductive ink containing from about 4 to about 12% by weight vapor grown carbon nanofibers having a high aspect ratio and at least one polymeric resin; and
applying said sensor to a structure to be monitored in the form of a grid pattern by painting, rolling, or spraying; and
providing a data acquisition system connected to said sensor for acquiring and evaluating data from said sensor.

8. The method of claim 7 wherein said structure is selected from a polymeric matrix composite structure, a metal structure, or a concrete structure.

9. The method of claim 7 wherein said structure comprises a polymeric matrix composite structure, and wherein said polymeric resin in said conductive ink is compatible with the polymer in said polymeric matrix composite structure.

10. The method of claim 7 wherein said structure comprises a polymeric matrix composite structure, and wherein said polymeric resin in said conductive ink is the same as the polymer in said polymeric matrix composite structure.

11. The method of claim 7 wherein said polymeric resin is selected from the group consisting of epoxy resins, polyimides, bismaleimides, cyanate esters, polyesters, vinyl esters, and urethanes.

12. The method of claim 7 wherein said data acquisition system comprises electrodes bonded to said sensor.

13. The method of claim 7 wherein said sensor is applied directly to said structure.

14. The method of claim 7 wherein said structure is electrically conductive.

15. The method of claim 14 including applying a nonconductive insulating coating to said structure prior to applying said sensor.

* * * * *